(12) United States Patent
Morris et al.

(10) Patent No.: US 11,986,286 B2
(45) Date of Patent: May 21, 2024

(54) GAIT-BASED ASSESSMENT OF NEURODEGENERATION

(71) Applicant: GaitIQ, Inc., San Antonio, TX (US)

(72) Inventors: Richard Morris, San Antonio, TX (US); Barbara Schnan Mastronardi, San Antonio, TX (US)

(73) Assignee: GaitIQ, Inc., San Antonio, TX (US)

( * ) Notice: Subject to any disclaimer, the term of this patent is extended or adjusted under 35 U.S.C. 154(b) by 0 days.

(21) Appl. No.: 16/948,166

(22) Filed: Sep. 4, 2020

(65) Prior Publication Data

US 2021/0059565 A1 Mar. 4, 2021

Related U.S. Application Data

(60) Provisional application No. 62/895,973, filed on Sep. 4, 2019.

(51) Int. Cl.
| | |
|---|---|
| A61B 5/11 | (2006.01) |
| A61B 5/00 | (2006.01) |
| G06N 20/00 | (2019.01) |
| G06T 7/73 | (2017.01) |
| G06V 20/40 | (2022.01) |
| G06V 40/20 | (2022.01) |

(52) U.S. Cl.
CPC .......... *A61B 5/112* (2013.01); *A61B 5/1127* (2013.01); *A61B 5/4082* (2013.01); *A61B 5/4088* (2013.01); *G06N 20/00* (2019.01); *G06T 7/74* (2017.01); *G06V 20/46* (2022.01); *G06V 40/25* (2022.01); *G06T 2207/10016* (2013.01); *G06T 2207/20081* (2013.01); *G06T 2207/30196* (2013.01); *G06T 2207/30204* (2013.01); *G06T 2210/22* (2013.01)

(58) Field of Classification Search
CPC .................. A61B 5/112; A61B 5/1128; A61B 5/4076–4088; G06K 9/00348
See application file for complete search history.

(56) References Cited

U.S. PATENT DOCUMENTS

| | | |
|---|---|---|
| 10,445,930 B1 | 10/2019 | Saylor et al. |
| 2014/0024971 A1* | 1/2014 | Bunn ................... A61B 5/1128 600/595 |
| 2014/0276130 A1 | 9/2014 | Mirelman et al. |
| 2016/0147959 A1 | 5/2016 | Mariottini et al. |

(Continued)

OTHER PUBLICATIONS

Begg, Rezaul, and Joarder Kamruzzaman. "A machine learning approach for automated recognition of movement patterns using basic, kinetic and kinematic gait data." Journal of biomechanics 38.3 (2005): 401-408. (Year: 2005).*

(Continued)

*Primary Examiner* — Vincent Rudolph
*Assistant Examiner* — Raphael Schwartz
(74) *Attorney, Agent, or Firm* — Schwegman Lundberg & Woessner, P.A.

(57) ABSTRACT

Neurodegeneration can be assessed based on a gait signature, using a machine-learning model trained on gait metrics acquired for a patient, in conjunction with cognitive test data and neuropathology information about the patient. The gait signature can be derived from gait kinematic data, e.g., as obtained with a video-based, marker-less motion capture system.

15 Claims, 11 Drawing Sheets

(56) References Cited

U.S. PATENT DOCUMENTS

2019/0110754 A1* 4/2019 Rao ................. G06N 5/022

OTHER PUBLICATIONS

Aziz, Wajid, and Muhammad Arif. "Complexity analysis of stride interval time series by threshold dependent symbolic entropy." European journal of applied physiology 98.1 (2006): 30-40. (Year: 2006).*

Corazza, Stefano, et al. "A markerless motion capture system to study musculoskeletal biomechanics: visual hull and simulated annealing approach." Annals of biomedical engineering 34.6 (2006): 1019-1029. (Year: 2006).*

Savica, Rodolfo, et al. "Comparison of gait parameters for predicting cognitive decline: the Mayo Clinic Study of Aging." Journal of Alzheimer's Disease 55.2 (2017): 559-567. (Year: 2017).*

Shetty, Sachin, and Y. S. Rao. "SVM based machine learning approach to identify Parkinson's disease using gait analysis." 2016 International Conference on Inventive Computation Technologies (ICICT). vol. 2. IEEE, 2016. (Year: 2016).*

Wennberg, Alexandra MV, Rodolfo Savica, and Michelle M. Mielke. "Association between various brain pathologies and gait disturbance." Dementia and geriatric cognitive disorders 43.3-4 (2017): 128-143. (Year: 2017).*

Devanne, Maxime, et al. "Learning shape variations of motion trajectories for gait analysis." 2016 23rd International Conference on Pattern Recognition (ICPR). IEEE, 2016. (Year: 2016).*

Rocha, Ana Patrícia, et al. "Parkinson's disease assessment based on gait analysis using an innovative RGB-D camera system." 2014 36th Annual International Conference of the IEEE Engineering in Medicine and Biology Society. IEEE, 2014. (Year: 2014).*

"International Application Serial No. PCT/US2020/070504, International Search Report dated Nov. 20, 2020", 2 pgs.

"International Application Serial No. PCT/US2020/070504, Written Opinion dated Nov. 20, 2020", 5 pgs.

Decker, Leslie M., et al., "Complexity and Human Gait", (2010), Journal Articles, 91, (2010), 25 pgs.

Ionescu, Catalin, et al., "Human3.6M: Large Scale Datasets and Predictive Methods for 3D Human Sensing in Natural Environments", IEEE Transactions on Pattern Analysis and Machine Intelligence, vol. 36, No. 7, pp. 1325-1339, Jul. 2014, doi: 10.1109/TPAMI.2013.248, (Jul. 2014), 1325-1339.

Martinez, Julieta, et al., "A simple yet effective baseline for 3d human pose estimation", Computer Vision Foundation, ICCV Open Access version, (Oct. 1, 2017), 2640-2649.

McCamley, John D., et al., "On the Calculation of Sample Entropy Using Continuous and Discrete Human Gait Data", Entrop 2018, 20, 764; doi:10.3390/e20100764, (Oct. 5, 2018), 20 pgs.

* cited by examiner

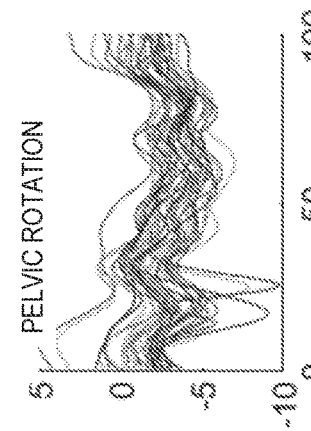
FIG. 9A
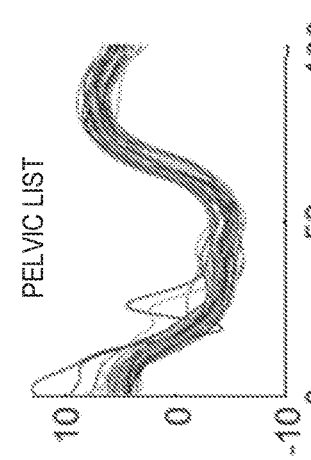
FIG. 9B
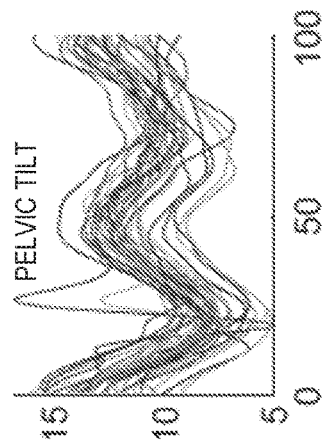
FIG. 9C
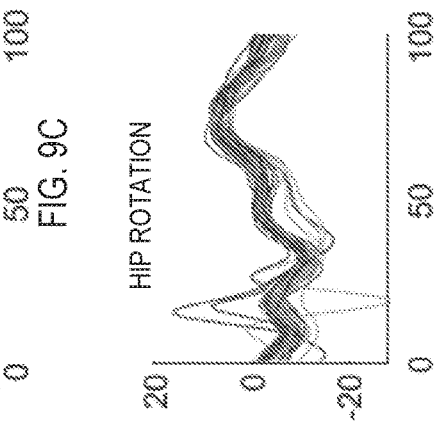
FIG. 9D
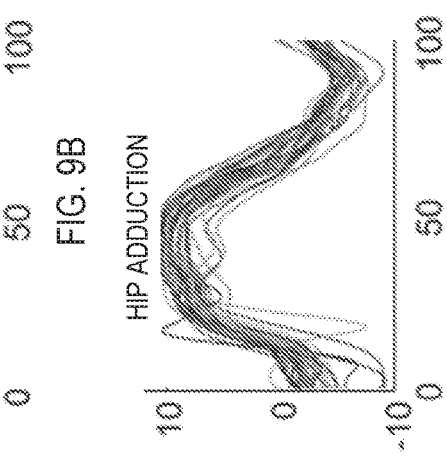
FIG. 9E
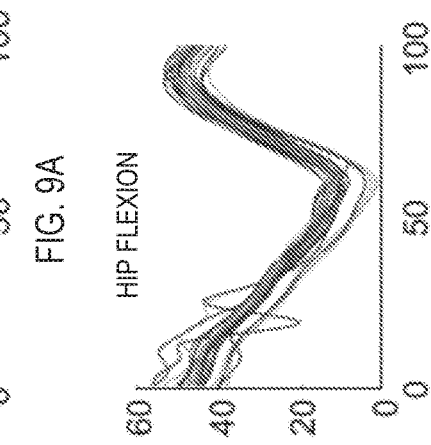
FIG. 9F
FIG. 9G
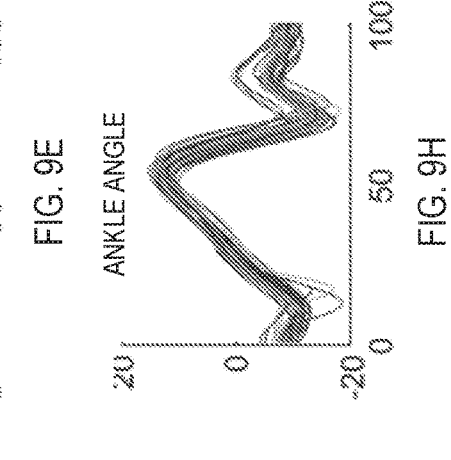
FIG. 9H
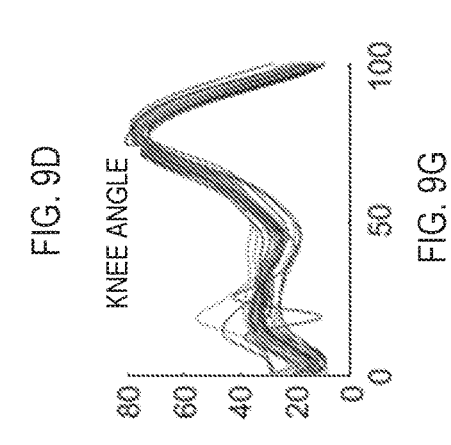

GAIT-BASED ASSESSMENT OF NEURODEGENERATION

CROSS-REFERENCE TO RELATED APPLICATION

This application claims priority to and the benefit of U.S. Provisional Patent Application No. 62/895,973, filed on Sep. 4, 2019, which is hereby incorporated herein by reference.

TECHNICAL FIELD

This application relates to gait as an indicator of neurodegenerative conditions, and specifically to gait-based diagnostic devices, systems, and methods.

BACKGROUND

Neurodegenerative conditions such as Alzheimer's disease, Lewy body dementia, and other forms of dementia, as well as Parkinson's disease, Huntington's disease, etc. often manifest themselves in changes to a patient's gait, sometimes years before other symptoms arise. Significant research has, therefore, been devoted in recent years to refine our understanding of the link between gait and neurodegeneration. Technology employed to measure gait includes the GAITRite® system, which uses a pressure-sensing mat, or "walkway," to measure the relative arrangements of the footfalls as a person walks across the mat, in conjunction with software to process the footfalls to derive certain spatiotemporal gait parameters, such as, e.g., stride length. While this system constitutes the current "gold standard" for gait measurements, it fails to capture, by its nature, the three-dimensional (3D) movements associated with walking, and is, furthermore, impractical and too costly to use in a clinical (and outside an academic) setting. An alternative approach utilizes marker-based motion capture, e.g., using the Vicon® system, in conjunction with a biomechanical model to derive kinematic parameters. While this approach can provide a more complete, 3D picture of a person's gait, it, too, places limits on its use in clinical applications, in part due to time-consuming processing of the marker-based data. As a result, the potential of gait as a diagnostic or early-stage screening tool for neurodegenerative conditions in a clinical context has not been realized to date.

SUMMARY

Disclosed herein is an approach for the gait-based assessment of neurodegenerative conditions that employs motion-capture functionality to derive gait metrics in conjunction with one or more machine-learning models to make predictions about the neurodegenerative condition based on the gait metrics. "Machine-learning models" are herein broadly understood to include any kind of computational model trained on data, rather than explicitly programmed, to perform a specified task; example of machine-learning models include, without limitation, decision trees, regression models, support vector machines, and artificial neural networks. In accordance with various embodiments, one or more software-implemented machine-learning models are trained on gait metrics correlated with some quantitative measure of a neurodegenerative condition as determined, e.g., using cognitive testing and/or neural imaging, for a number of people. Once trained, the model(s) may predict the likelihood that a neurodegenerative condition, such as e.g., Alzheimer's disease or some other form of dementia, is present (or will develop) in a person, or quantify a degree to which a neurodegenerative condition is present, such as, e.g., a heightened fall risk. The gait metrics that flow as input into the model(s) may be derived (e.g., by state space examination, approximate entropy analysis, detrended fluctuation analysis, principal component analysis, or other techniques) from gait kinematic data including times-series kinematic parameters of joints and body segments and/or spatiotemporal parameters derived from such time-series data. In some embodiments, training of the model involves determining a subset of gait metrics that correlate strongly with the neurodegenerative condition and can collectively be used as a "gait signature." In addition to the gait signature, the model may take patient demographic data or personal health information as input.

The gait kinematic data from which the gait metrics are derived can in principle be obtained with a marker-based or marker-less motion captures system. In various beneficial embodiments, gait kinematic data is determined without the need for markers by processing video data of a person captured as the person is walking with a computational (e.g., machine-learning) motion-analysis model.

The approach described herein closes the gap between research results generally linking gait to neurodegenerative conditions and a diagnostic tool that can be used in clinical practice. In particular when utilizing low-cost video-based motion capture, the described approach describes a fast and inexpensive means of assessing a patient for neurodegenerative conditions, suitable for routine testing and screening.

BRIEF DESCRIPTION OF THE DRAWINGS

The foregoing will more readily understood from the following detailed description of various example embodiments, in particular, when taken in conjunction with the drawings, in which:

FIGS. 9A-9H are graphs illustrating example joint-angle signals, segmented by strides and overlaid, in accordance with various embodiments.

DETAILED DESCRIPTION

Described herein are systems, methods, and computer program products as embodied in computer-readable media that facilitate testing for and assessing neurodegenerative conditions based on a patient's gait. In general, the disclosed approach can be implemented by a processing facility that includes a suitable combination of hardware and/or software, in conjunction with suitable video-capture hardware, such as one or more video cameras. The processing facility may generally include one or more general-purpose processors (e.g., a central processing unit (CPU) or graphics processing unit (GPU)) or special-purpose processors (e.g., a digital signal processor (DSP), application-specific integrated circuit (ASIC), etc.). In some embodiments, the processing facility includes one or more (e.g., a cluster of) computers executing software instructions stored in computer memory.

Figure 1:
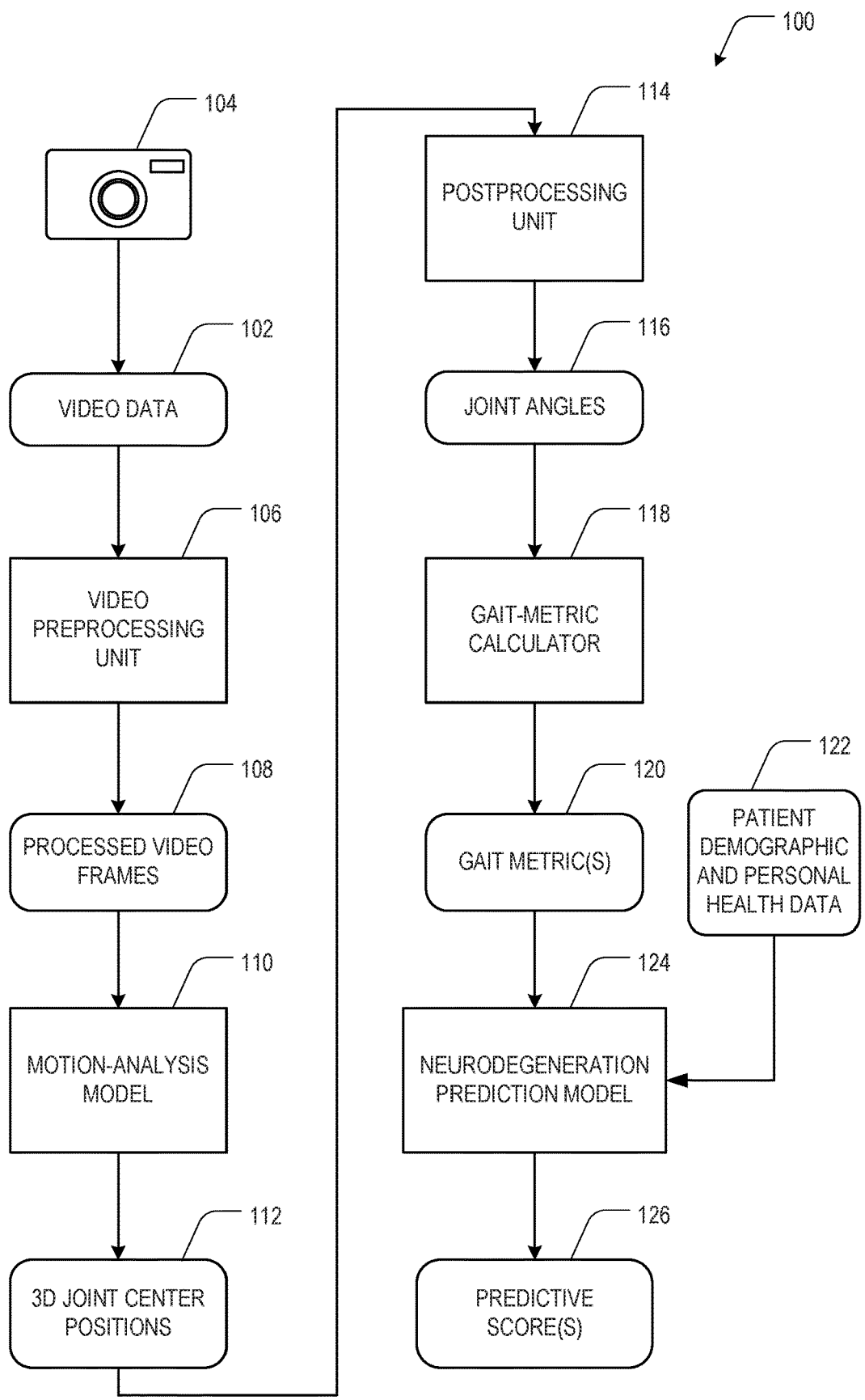
FIG. 1 is a data flow diagram illustrating an example system for the gait-based assessment of neural degeneration, including a motion-analysis model to compute gait metrics followed by a neurodegeneration prediction model operating on the gait metrics, in accordance with various embodiments.

FIG. 1 is a data flow diagram illustrating an example system 100, including processing components and computational models (shown as rectangles with sharp corners) and their respective data inputs and outputs (shown as rectangles with rounded corners), for the gait-based assessment of neural degeneration, in accordance with various embodiments. The system 100 captures a subject's, such as a patient's, movements with marker-less motion capture technology, based on high-definition video data 102 of the patient acquired by one or more (e.g., optical) cameras 104, which may be standard cameras, including, e.g., cameras as typically integrated into smartphones and other handheld computational devices. Beneficially, with the processing functionality described herein, even video from only a single camera can be processed to derive 3D motion data. Eliminating the need for multiple synchronized cameras makes gait measurements accessible, from a practical and economic standpoint, to a broad user base. A physician, such as a general practitioner, may, for instance, use simply the built-in camera of a smartphone, tablet, or similar consumer electronic computational device to record video of a patient walking a short distance in his office, e.g., along a straight diagonal line in the field of view or in circles. The video can then be analyzed with software implementing the methods described herein to obtain a gait-based assessment of the patient's neural condition and/or risk of developing neural degeneration. No expensive custom hardware is needed. Multiple cameras 104 may, however, optionally be used, where feasible, to capture video simultaneously from multiple angles to provide 3D input for more accurate motion measurements. The video data 102 is processed by a sequence of processing components that may generally be software-implemented, although hardware accelerators may also be used. The software can, in some embodiments, run on the same computational device that, via an integrated camera 104, acquires the video data 102, or, alternatively, on a separate computer or cluster that receives the video data 102 via a wired or (usually) wireless network connection.

The processing components may include a video preprocessing unit 106 that serves to detect the subject in each video frame, crop the image around the subject, and resize the cropped image to a fixed size used as input in the next stage, as explained in more detail below with reference to FIG. 2. The preprocessed video frames are fed into a trained machine-learning model for motion analysis, hereinafter the "motion-analysis model" 110, which computes certain gait kinematic parameters. The motion-analysis model 110 may be, e.g., a neural-network model, and training may be accomplished using data from a marker-based system as the ground-truth, as detailed below with reference to FIG. 10.

Gait kinematic parameters (also collectively "gait kinematic data"), as herein understood, are time-dependent (i.e., if digital, time-series) kinematic parameters associated with joints and/or body segments, especially those of the lower extremities (although kinematic parameters of upper-body joints and segments may also be included). Kinematic parameters include linear (translational) and/or angular (rotational) positions, velocities, and/or accelerations, each measured with respect to a coordinate system fixed in space or relative to other body parts (e.g., pelvic tilt, pelvic list, pelvic rotation, hip abduction, hip flexion, hip rotation, left and right knee angles, left and right ankle angles, T1 head neck axial rotation, T1 head neck flexion/extension, T1 head neck lateral bending, thoracic axial rotation, thoracic flexion/extension, thoracic lateral bending, left and right shoulder elevation, left and right elbow flexion, left and right wrist flexion), as well as spatiotemporal parameters computed from the beforementioned "raw" parameters, such as, e.g., stride length (defined as the distance between successive points of heel contact of the same foot), step length (defined as the distance between successive points of heel contact of opposite feet), average speed, step frequency, etc.

In various embodiments, gait kinematic parameters are determined in two stages. First, as shown in FIG. 1, 3D joint center positions 112 as a function of time are determined as a direct output of the motion-analysis model 110. Then, a postprocessing unit 114 calculates joint angles 116, again as a function of time, from the joint center positions 112. Joint center positions 112 and joint angles 116 are both examples of gait kinematic parameters. In some embodiments, the postprocessing unit 114 reduces noise and removes outliers from the joint center positions 112 output by the motion-analysis model 110 before calculating the joint angles 116.

The joint angles 116 are further processed, using a processing module herein referred to as "gait-metric calculator" 118, to compute one or more gait metrics 120 that can serve as biomarkers for neurodegeneration. For example, healthy human gait has been found to exhibit complex, chaotic fluctuations indicative of a capability to make flexible adaptations to everyday stresses, whereas unhealthy gait is often characterized by either highly periodic fluctuations corresponding to increased rigidity or highly random fluctuations corresponding to instability, both of which decrease the ability to adapt to stresses and perturbations. Processing the joint angles 116 (or other gait kinematic parameters) may involve splitting time-dependent signal representing the joint angles 116 into strides and performing stride outlier detection and removal before calculating the gait metrics 120.

One or more gait metrics 120 computed for the patient, optionally along with patient demographic data (e.g., age, gender, race) or personal health information (e.g., smoker/ non-smoker, diabetic/non-diabetic, weight, height, etc.) 122, are used as input to a second trained machine-learning model, the "neurodegeneration prediction model" 124, which computes a predictive score 126 (or multiple such scores) associated with a neurodegenerative condition. The predictive score 126(s) may, for instance, provide the probability that the patient suffers from a certain condition (which may be, in the absence of symptoms, a risk of developing symptoms associated with the condition). The predictive score(s) 126 may also quantify a known existing condition, e.g., in the case of a heightened fall risk, the level of that risk.

The neurodegeneration prediction model 124 can generally be implemented with any of a variety of machine-learning-based linear and non-linear classifier techniques, including, but not limited to, e.g., Logistic Regression, Decision Trees, Boosted Trees, Random Forests, Naïve Bayes classifier, Nearest Neighbor algorithms, Support Vector Machines, Artificial Neural Networks (e.g., Deep Neural Networks), and other models and algorithms known to those of skill in the art. Principal Component Analysis may be used to reduce the number of parameters input into the model. The neurodegeneration prediction model 124 may also be an ensemble combining multiple individual models and suitably merging their predictions. Different machine-learning models may be used for different neurodegenerative conditions.

The neurodegeneration prediction model 124 may be trained in a supervised manner based on gait metrics correlated with ground-truth indicators of the patient's neurological condition, as explained in more detail below with reference to FIG. 11. Among an initially large number of possible gait metrics, one or more that correlate highly with neurodegenerative conditions in general, or a particular condition of interest (e.g., Alzheimer's disease), may be selected to collectively form a (disease-specific or condition-specific) gait signature. The selection may in principle be made by a human based on heuristics. In various embodiments, however, the selection is made in the course of training the neurodegeneration prediction model 124, e.g., using feature reduction techniques as are known to those of ordinary skill in the art. Once the set of gait metrics that constitute a useful gait signature has been determined, the trained neurodegeneration prediction model 124 need operate only on that set of gait metrics, and the gait-metric calculator 118, accordingly, need only calculate those metrics.

As will be appreciated by those of ordinary skill in the art, the operation of the neurodegeneration prediction model 124 is generally independent of the way in which the gait kinematic data (e.g., 3D joint positions 112 and/or joint angles 116) from which the gait metrics 120 are computed is acquired (assuming that the data 112, 116 is sufficiently accurate). Accordingly, while marker-less, video-based motion capture is beneficial due to its low hardware requirements and simplicity, e.g., from a healthcare provider's perspective, marker-based and other motion capture approaches may also be utilized as subsystems within system 100. In fact, in accordance with various embodiments, marker-based motion capture technology, e.g., the Vicon® motion capture system by Vicon Motion Systems (headquartered in Yarnton, Oxfordshire, UK), provides the ground-truth for training a video-based motion capture system as implemented by the motion-analysis model 110, in conjunction with the camera(s) 104 for providing the raw video input and with the pre- and postprocessing units 106, 114.

Marker-less and marker-based motion capture generally constitute alternative ways to generate the gait kinematic data 112, 116, but may also be used in conjunction, e.g., to improve accuracy. Further, other motion-capture technologies, such as active optical systems that utilize, instead of reflectors, light-emitting diodes integrated into a body suit worn by the patient, or systems of patient-worn inertial sensors that measure accelerations and transmit their data wirelessly to a computer, may also in principle be used.

In the following, various components of the system 100 for the gait-based assessment of neurodegeneration and their operation are described in more detail.

Figure 2:
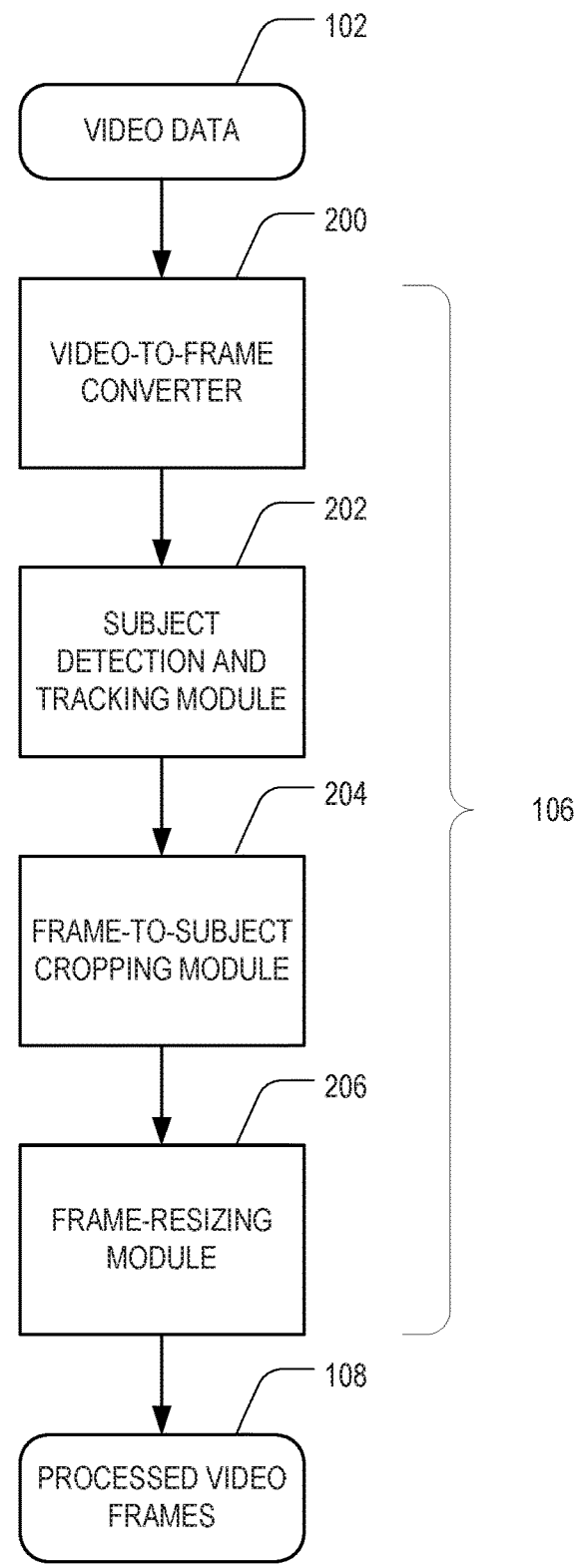
FIG. 2 is a data flow diagram illustrating the preprocessing of video data to generate input to the motion-analysis model of FIG. 1, in accordance with an example embodiment.

FIG. 2 is a data flow diagram illustrating the preprocessing of video data 102, by preprocessing unit 106, to generate input to the motion-analysis model 110 of FIG. 1, in accordance with an example embodiment. To measure a patient's gait, video data 102 is captured, in accordance herewith, as the patient is walking, e.g., for periods of several seconds or tens of seconds, completing multiple strides. The patient may be directed to walk at a self-selected pace, or at a relatively slow or fast pace, and may be asked to simultaneously perform certain other, typically cognitive tasks (e.g., counting backwards).

In the embodiment depicted in FIG. 2, the raw video data 102 is processed through a video-to-frame converter 200, which is an important step if the motion-analysis model 110 processes one single frame at a time, as is the case in various embodiments. The individual frames are then processed through a subject detection and tracking module 202. During this stage, the patient is detected in the frames, and the coordinates of a rectangular region containing the patient are determined. Subject detection in the first frame of a video may take place automatically (e.g., using human detection models) or manually (e.g., with a user selecting a rectangle around the subject). After detection in the first frame, the subject may be tracked through the remaining frames using an object tracking method, e.g., based on a technique known as the "discriminative correlation filter with channel and spatial reliability algorithm."

Given the coordinates of the image region containing the subject, as determined in the previous step, the frames are processed by a frame-to-subject cropping module 204, which will crop a square (or rectangle of specified aspect ratio) around the detected subject. The subsequent analysis will be applied only to this region, and the remaining portion of the image, which cannot provide any information about the subject himself, is removed from the assessment, saving the computational cost otherwise associated with involved, yet unnecessary computations. In addition to reducing the space of the subsequent analysis, cropping also serves to normalize the size of the subject in the image, which standardizes the size of the relevant features inside the image, improving recognition accuracy and decreasing the relevance of other attributes (e.g., distance of the subject to the camera, physical height of the subject, etc.).

The cropped image may be shrunk, by a frame resizing module 206, to satisfy the minimum dimensions specified for the input to the motion-analysis model 110. In some embodiments, if the cropped image is too small to reach or exceed these minimum dimensions (e.g., as a result of a patient being to far away from the camera 103), the image is not used in further analysis, which avoids potentially significant error that would otherwise be added during the motion analysis as a result of image expansion. The cropped images constitute the processed video frames 108 provided as input to the motion-analysis model 110.

Figure 3:
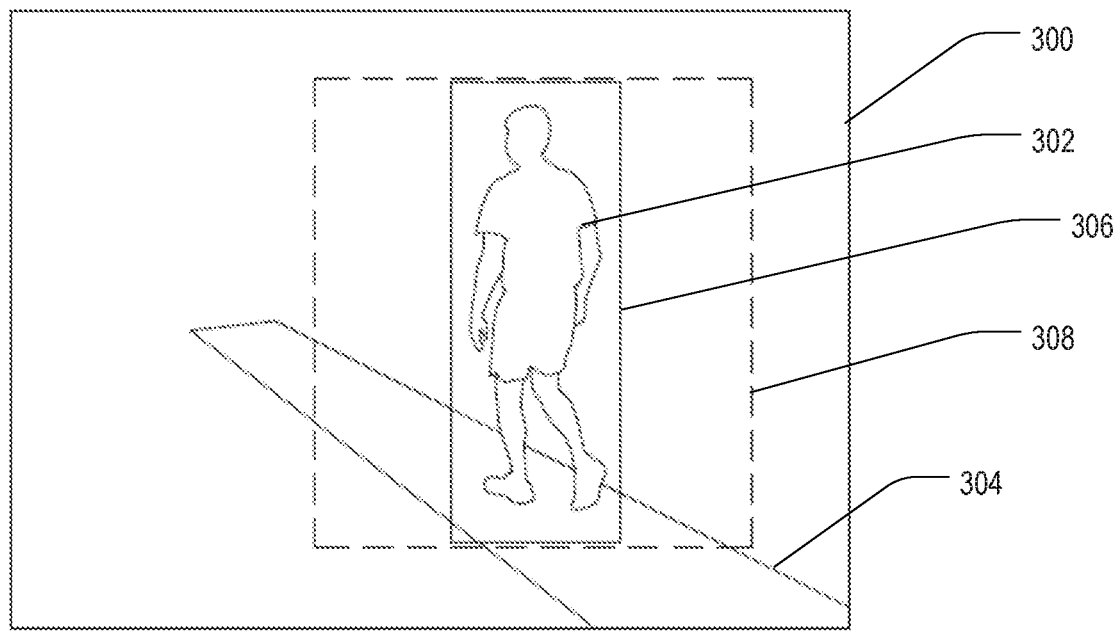
FIG. 3 is a schematic line drawing of an example video frame, illustrating image cropping as part of the preprocessing depicted in FIG. 2.

FIG. 3 is a schematic line drawing of an example video frame 300, illustrating image cropping as part of the preprocessing depicted in FIG. 2. In the video frame 300, a patient 302 can be seen walking along a walkway 304. In accordance with the processing steps described above, a rectangular region 306 surrounding the subject can be identified during subject detection, followed by cropping a normalized square region 308 around the rectangular region 306.

In various embodiments, the motion-analysis model 110 includes a CNN that includes convolutional layers and fully connected layers, which serves to detect relevant features in, and extracts them from, the input processed video frames 108. In addition, the model 110 may apply Long Short-Term Memory (LSTM) networks to incorporate temporal motion dependency between frames, an important function given that each frame in a video is related to its previous and following frames. In one example embodiment, the input of the model 110 is a square image of 368 pixels in each width and height, and the output is a list of joint center positions in a 3D coordinate system. This way, each frame is processed to create a new data point (x, y, z) for each joint; the data points produced in each frame are combined to create a signal-type time-series data set for each joint. The output data may be organized in a co-moving coordinate system having its origin at the center of the patient's pelvis (or some other reference point fixed relative to the patient), the remaining joints being positioned relative to the center of the pelvis.

Figure 4:
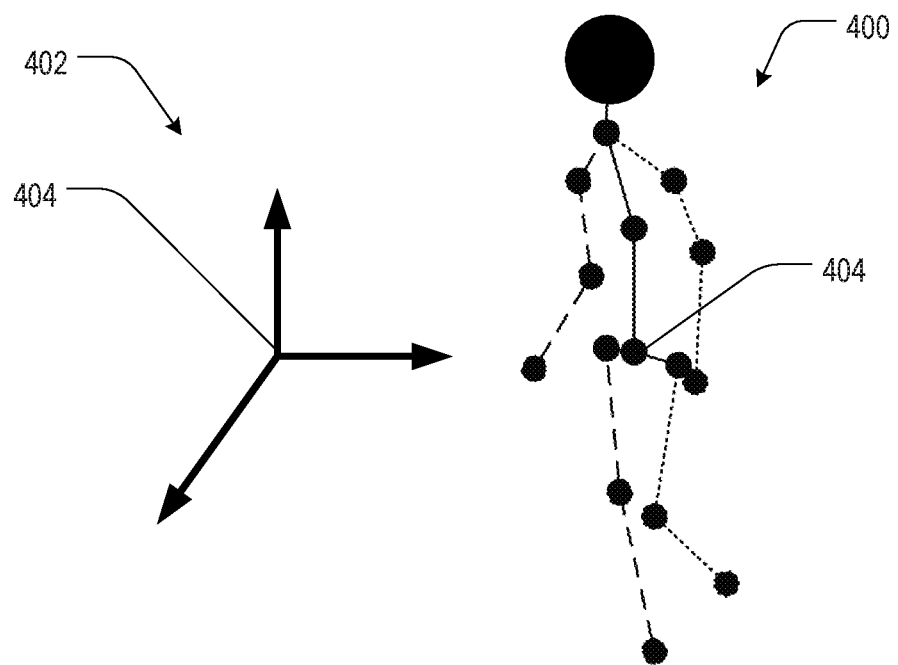
FIG. 4 is an example skeleton representation illustrating 3D joint positions output by the motion-analysis model of FIG. 1, in accordance with various embodiments.

FIG. 4 is an example skeleton representation 400 illustrating 3D joint positions output by the motion-analysis model 110 of FIG. 1, in accordance with various embodiments. To avoid obfuscating the drawing, the coordinate system 402 is shown alongside the skeleton representation 400; the origin 404 of the coordinate system 402 is, in actuality, located at the center of the patient's pelvis. The skeleton representation 400 graphically represents the positions of various body parts and joints and the connecting segments therebetween. In the depiction, the patient's head and torso are connected by solid lines, whereas the patient's right and left extremities are shown in dashed and dotted lines, respectively.

Figure 5:
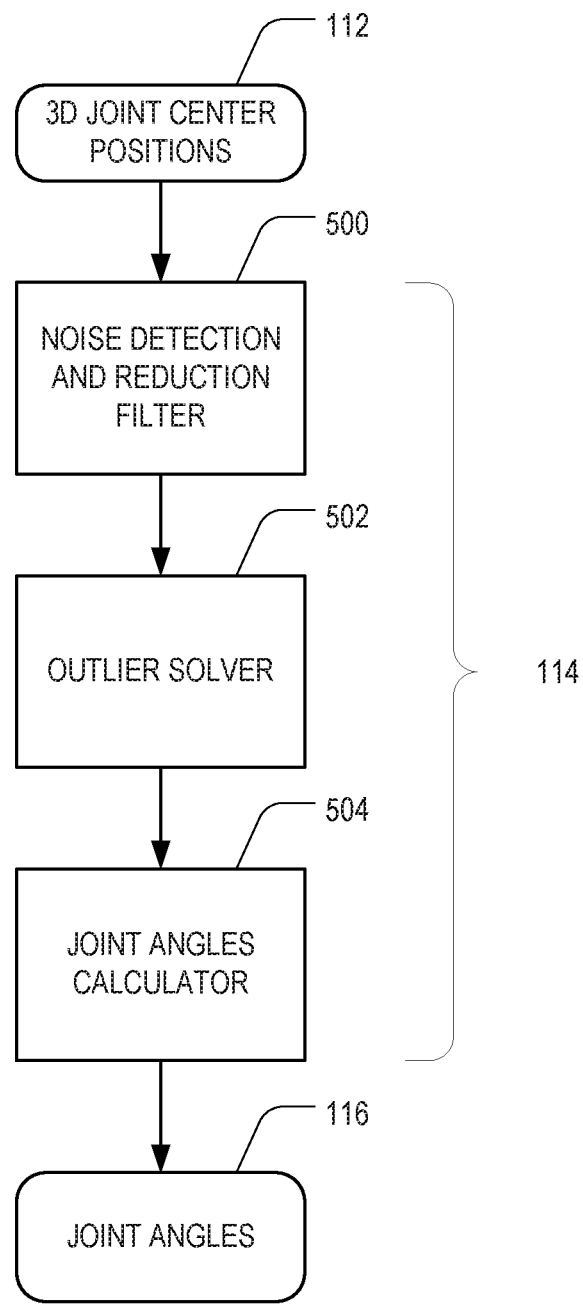
FIG. 5 is a data flow diagram illustrating the post-processing of 3D joint positions to compute joint angles, in accordance with an example embodiment.

FIG. 5 is a data flow diagram illustrating the postprocessing, by postprocessing unit 114, of 3D joint positions 112 to compute joint angles 116, in accordance with an example embodiment. The 3D joint positions 112 output by the motion-analysis model 110 are first processed by a noise detection and reduction filter 500 to remove interference and smooth the signal produced for each joint. Algorithms applied in this module may include a Savitzky-Golay filter, among others. The subsequent outlier solver 502 detects atypical data points in the joint signal, not solved by the previous filter 500. If the outliers occur at the extremes of the curve (start or end), these data points are not used in the following module and, thus, removed from the signal. If the outliers occur in the middle of the curve, linear interpolation is used to generate a new value in the outlier's place based on the surrounding data points. A joint angles calculator 504 then operates on the filtered or smoothed 3D joint center positions 112 to produces joint angles 112 for each joint. The angles produced by this calculator 504 may include, but are not limited to, knee flexion/extension, hip flexion/extension and abduction/adduction, pelvic obliquity and rotation, shoulder flexion/extension and abduction/adduction, and elbow flexion/extension.

Figure 6A:
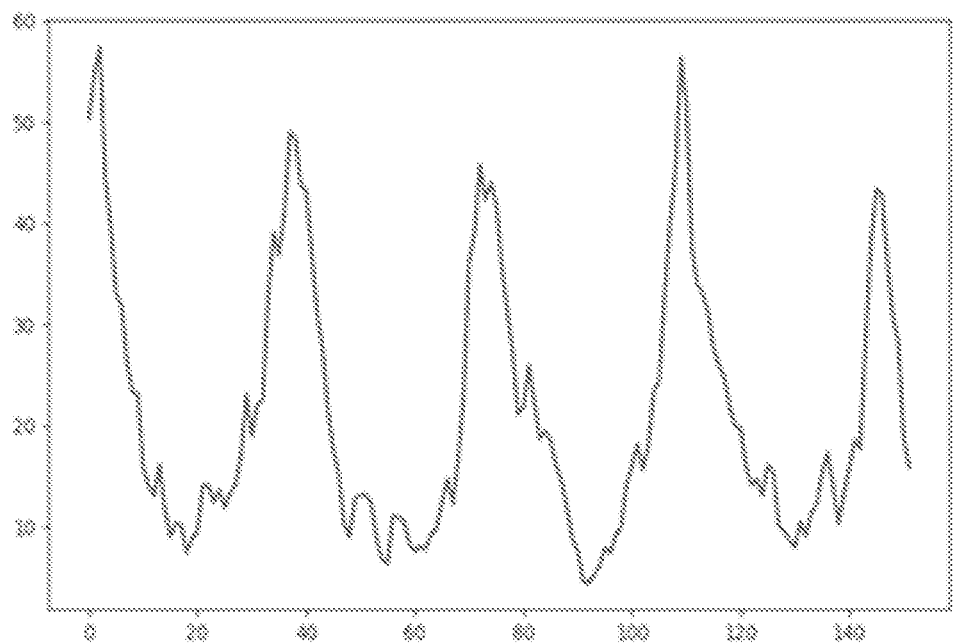
FIGS. 6A and 6B are graphs of a joint-angle signal before and after noise filtering and outlier removal in accordance with an example embodiment.
Figure 6B:
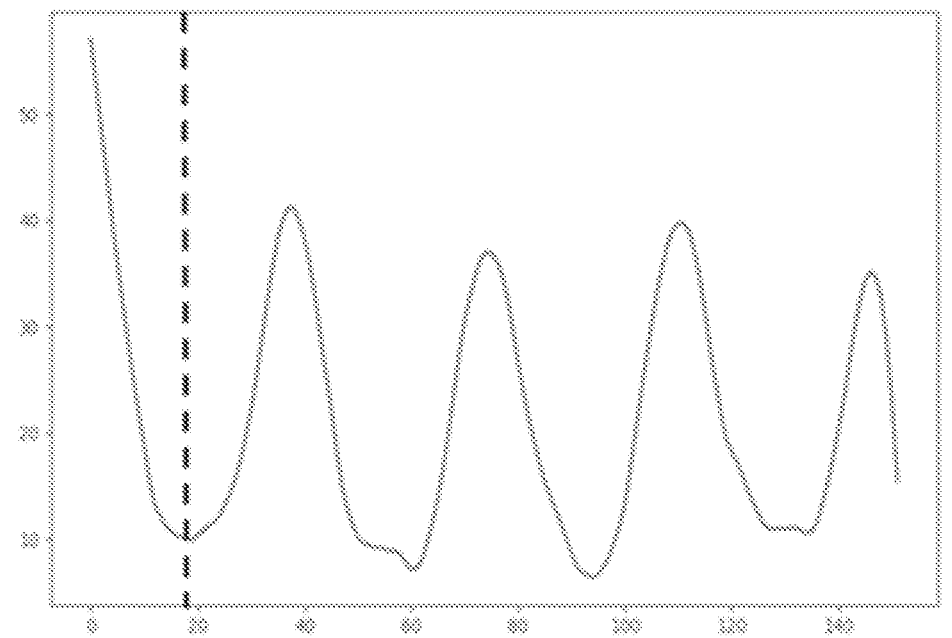

FIGS. 6A and 6B are graphs of a joint-angle signal before and after noise filtering and outlier removal, respectively, in accordance with an example embodiment. In the graphs, a joint angle is plotted (in arbitrary units) as a function of time (likewise in arbitrary units). The periodic nature of the curves reflects repetitive motions corresponding to strides; four full strides are shown. Noise filtering is applied over the entire signal shown in FIG. 6A, resulting in substantial smoothening, as can be seen in FIG. 6B. Outliers are removed from the beginning of the signal up to the dotted line drawn in FIG. 6B.

Figure 7:
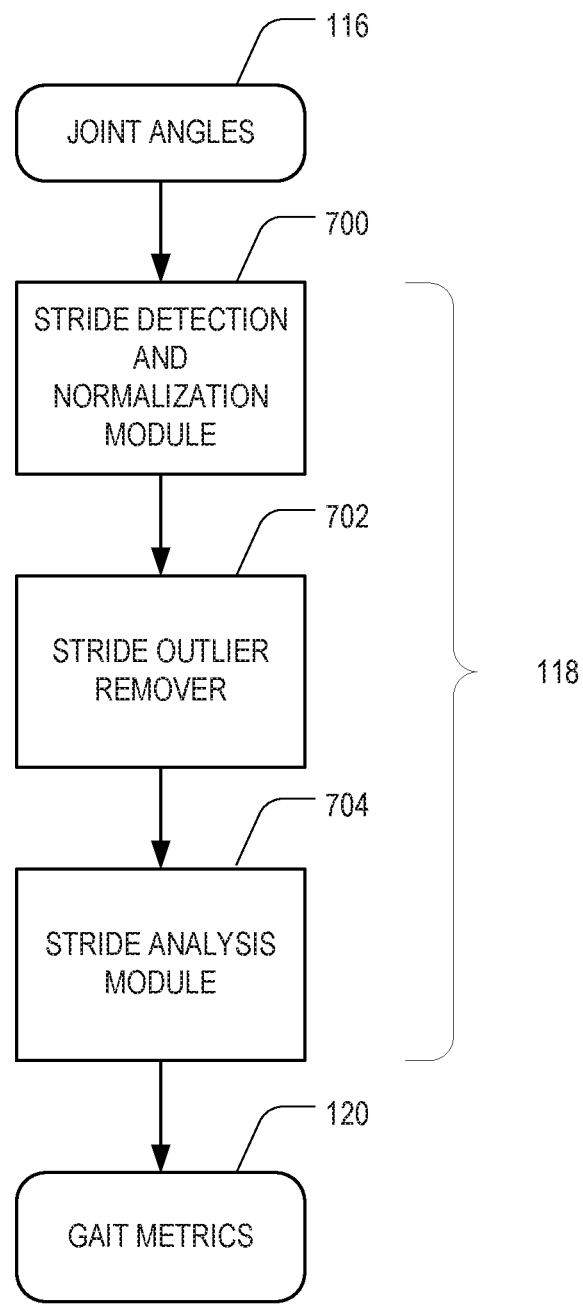
FIG. 7 is a data flow diagram illustrating the computation of gait metrics from joint angles, in accordance with an example embodiment.

FIG. 7 is a data flow diagram illustrating the computation, by the gait metric calculator 118, of gait metrics 114 from joint angles 116, in accordance with an example embodiment. A stride detection and normalization module 700 analyzes the periodic joint-angle signals to find the beginning of each stride and normalizes the time length of the stride to a percentage range (1%-100%). A new stride can be detected with different techniques, for example, by locating certain characteristic features in the curve, such as the lowest point of the joint-angle signal for the left or right ankle joint, or the maximum extension of the right or left knee angle. With this time information, each joint-angle signal can be divided into strides. The time normalization allows the comparison between strides independently of their time length, that is, the data for all strides includes the same number of data points, which focuses the analysis on the morphology of the stride. The stride outlier remover 702 takes the whole set of strides (for each joint), and identifies atypical ones. This process can be done using techniques like "distance to the median stride," where a stride that is located at a certain distance from the median is considered an outlier. The stride analysis module 704 takes the set of strides for each joint angle delivered by the previous module, and calculates one or more gait metrics 120.

Figure 8A:
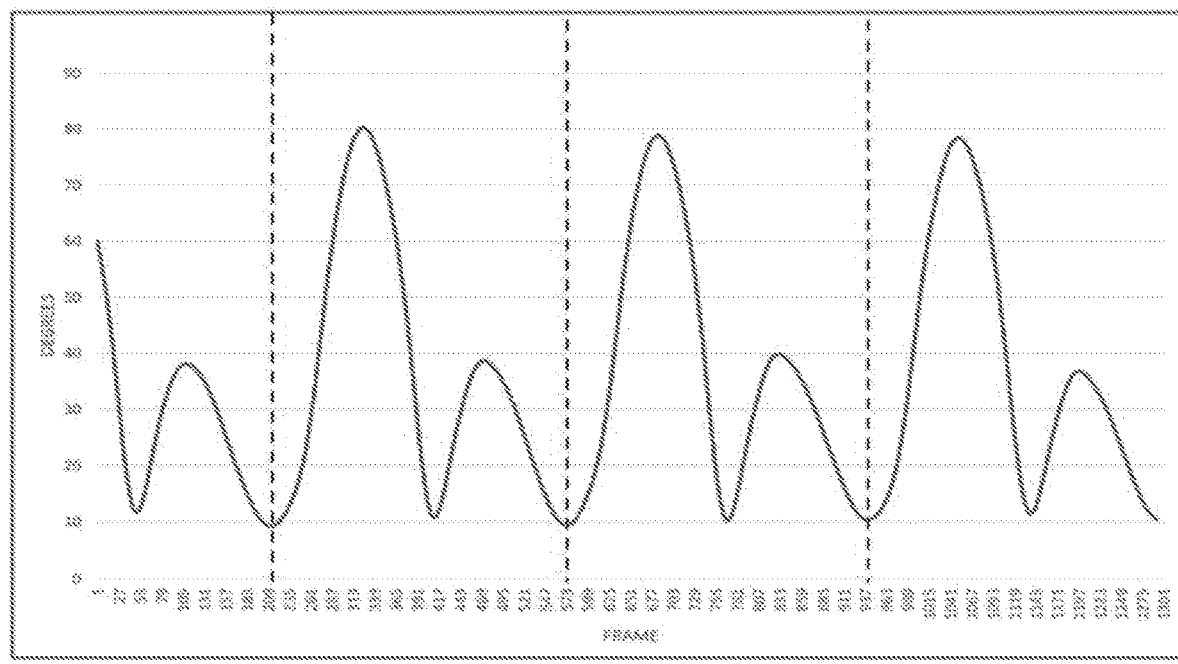
FIGS. 8A and 8B are graphs illustrating an example knee-angle signal and an overlay of curve segments for multiple strides within that signal, in accordance with various embodiments.
Figure 8B:
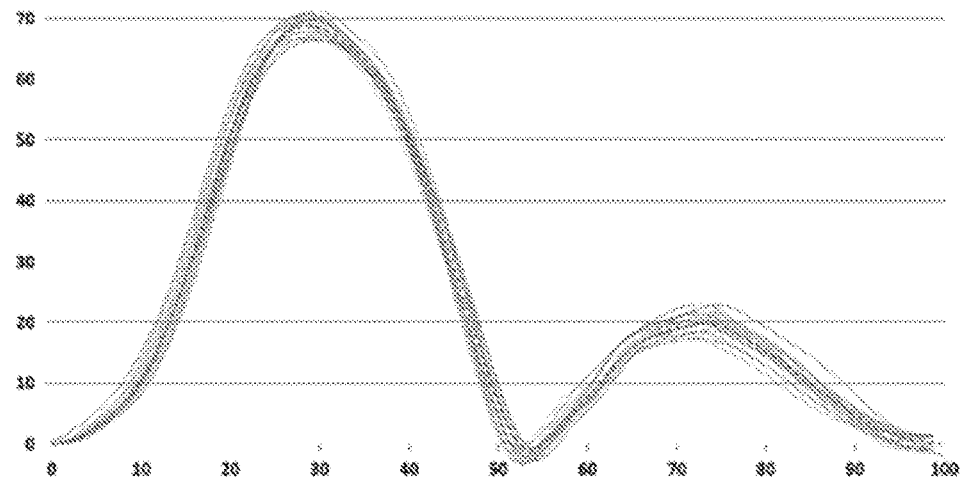

FIGS. 8A and 8B are graphs illustrating an example knee-angle signal and an overlay of curve segments for multiple strides within that signal, in accordance with various embodiments. Stride detection is based, in this case, on the maximum extension of the knee (corresponding to the smallest knee flexion angle), indicated by dashed lines in FIG. 8A. FIG. 8B illustrates good consistency in knee extension across multiple strides.

FIGS. 9A-9H are graphs illustrating various example joint-angle signals, segmented by strides and overlaid, in accordance with various embodiments. The depicted overlays of joint angles determined for sequences of successive strides illustrate both the general repetitiveness as well as the degree of variability between strides. The joint angles shown in FIGS. 9A-9H are pelvic tilt, pelvic list, pelvic rotation, hip flexion, hip adduction, hip rotation, knee angle, and ankle angle, respectively. As can be seen, each of these parameters has its own characteristic shape, and gait abnormalities, e.g., as resulting from neurodegenerative conditions, will generally be reflected in deviations from the usual characteristics.

The human gait, as mentioned above, is usually very complex, but an unhealthy gait can exhibit highly periodic fluctuations corresponding to increased rigidity or highly random fluctuations corresponding to instability, both of which correspond to reduced complexity. Accordingly, gait complexity provides a good biomarker for neurodegeneration. The complexity of a patient's gait can be evaluated in different ways and captured in different corresponding metrics, including Sample Entropy, Multi-Scale Entropy, and GaitSD. Further metrics can be derived by self-similarity evaluations of the time-series kinematic parameters, or state space examination (which represents the dynamics of joint movements in an abstract, multi-dimensional space spanned by state variables, such that a sequence of states corresponds to a curve in the multi-dimensional space), which are described in detail, for example, in a 2010 journal article by L Decker et al., entitled "Complexity and Human Gait" (published by the University of Nebraska, Omaha, Department of Biomechanics), which is herein incorporated herein by reference.

Figure 10:
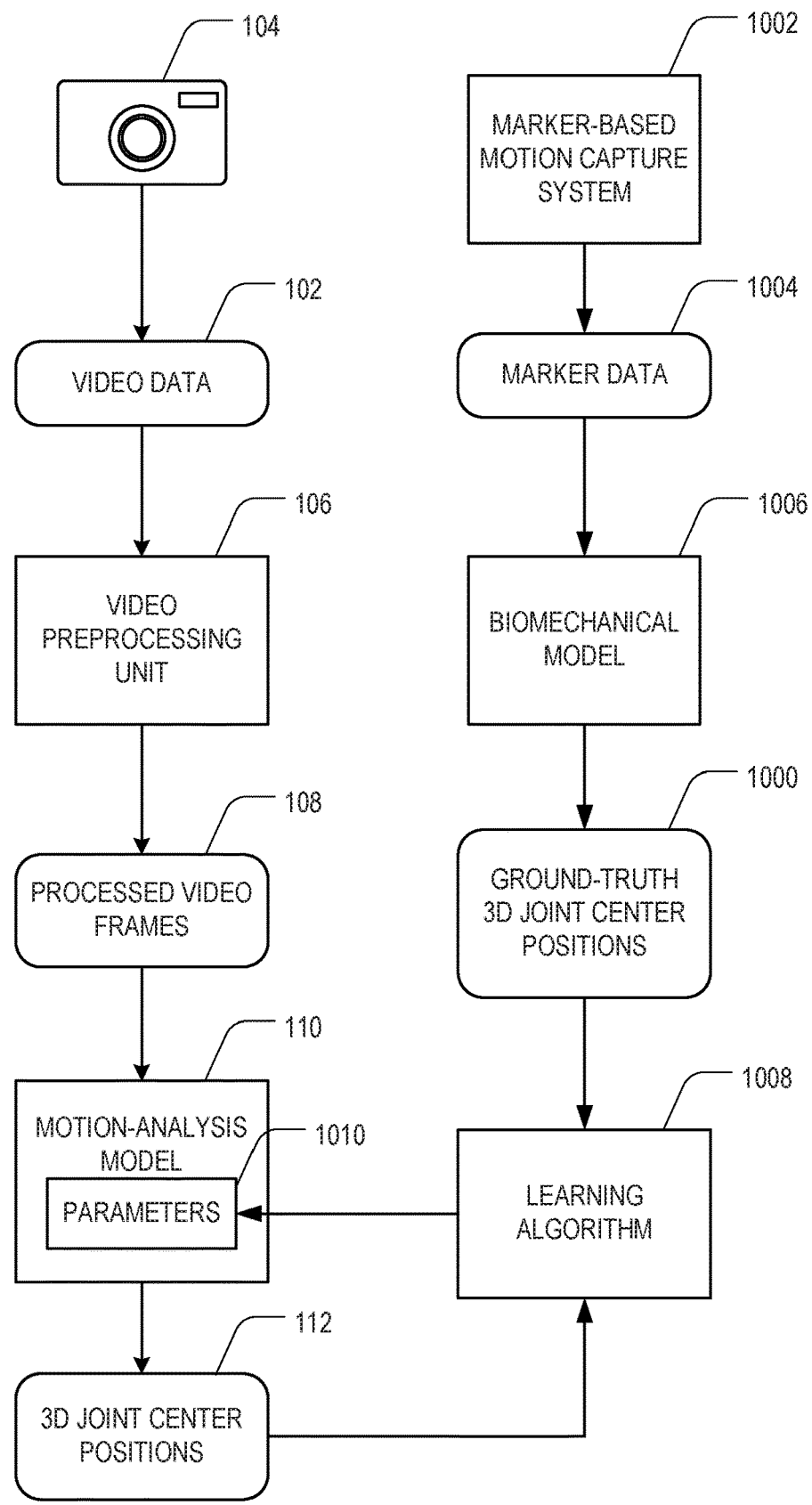
FIG. 10 is a data flow diagram illustrating supervised training of the motion-analysis model of FIG. 1, in accordance with various embodiments.

FIG. 10 is a data flow diagram illustrating supervised training of the motion-analysis model 110 of FIG. 1, in accordance with various embodiments. During training, just like during a subsequent inference phase, video data 102 captured by one or more cameras 104 is preprocessed (e.g., by video preprocessing unit 106), and, from the processed video data 108, the motion-analysis model 110 computes gait kinematic parameters such as, e.g., in the first instance, 3D joint center positions 112. This model output is compared against ground-truth 3D joint center positions 1000. The ground-truth data may be obtained, e.g., using a marker-based motion capture system 1002. For marker-based passive optical motion capture, retroreflective markers are attached to the patient, e.g., via skin-tape adhesive, at multiple specified locations on the body (e.g., on the knees, ankles, shin, thigh, toes, etc.), and their positions are tracked by (typically infrared) cameras, and fed as marker data 1004 into a biomechanical computational model 1106 to compute the 3D joint center positions 1000. The Vicon® motion capture system by Vicon Motion Systems (headquartered in Yarnton, Oxfordshire, UK) is an example of a commercially available system utilizing this approach. The video data 102 that provides the input to the motion-analysis model 110 and the marker video data are acquired simultaneously, such that the model input is correlated with the ground-truth output. Accordingly, a comparison of the 3D joint center positions 112 predicted by the motion-analysis model 110 against the marker-based ground-truth 3D joint center positions provides information about the accuracy of the model 110. In a supervised learning approach, a learning algorithm 1008 adjusts the motion-analysis model 110 (e.g., iteratively) minimize the discrepancy between predicted and ground-truth joint center positions (or other gait kinematic parameters). For example, a motion-analysis model implemented by a neural network may be trained using backpropagation of errors with gradient descent to iteratively adjust certain free parameters 1010 of the model 110. Once the motion-analysis model 110 has reached sufficient prediction accuracy for the intended purpose, the parameters 1010 are fixed, and the now trained model 110 is ready for use.

As will be appreciated, supervised training need not necessarily rely on marker-based systems to provide ground-truth data. As an alternative, a walkway equipped with pressure sensors may be used to measure the footfalls of a person walking, and the motion-analysis model 110 may be modified, or its outputs be further processed, to also provide footfall measurements, allowing the model 110 to be trained using the walkway-based measurements as ground-truth data within the training set. Other examples may occur to those of ordinary skill in the art.

Figure 11:
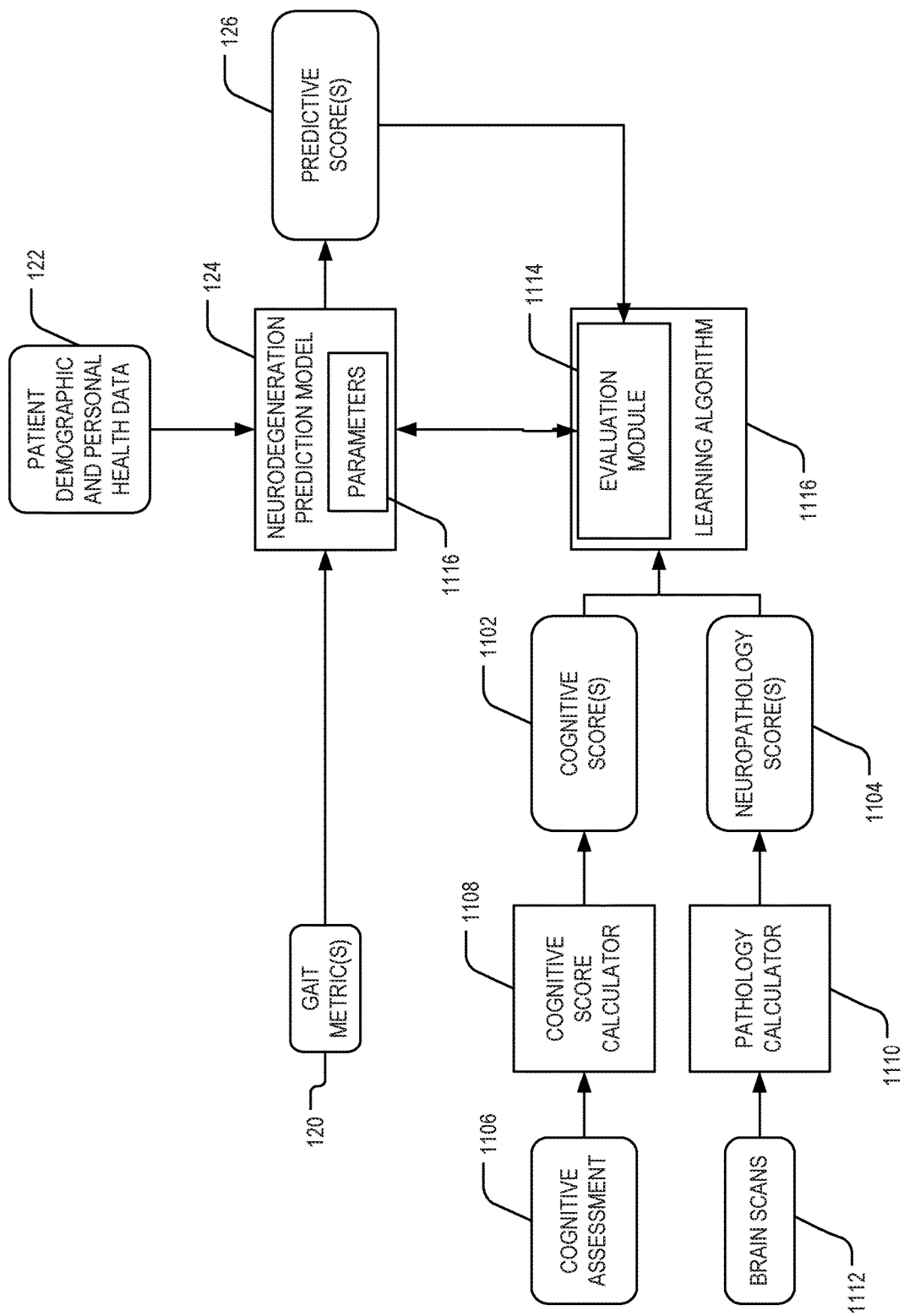
FIG. 11 is a data flow diagram illustrating supervised training of the neurodegeneration prediction model of FIG. 1, in accordance with various embodiments.

Turning now to FIG. 11, the training of a neurodegeneration prediction model 124 operating on gait metrics 120 is illustrated in a data flow diagram. The training data includes sets of gait metrics 120 as derived in the above-described manner from gait kinematic data 112, 116 acquired for many (e.g., a hundred or more) patients, each set paired with evaluation scores quantifying the neurodegenerative condition for the respective patient, which serve as the ground truth for supervised learning of the model 124. The evaluation scores may include one or more cognitive scores 1102 and one or more neuropathology scores 1104. To obtain the cognitive score(s) 1102, the patient may be subjected to a cognitive assessment 1106 involving, e.g., a battery of cognitive tests, and a cognitive-score calculator 1108 (e.g., implemented in software) may compute scores from the test results; the individual scores for multiple cognitive tests may be aggregated into a single composite cognitive score. The neuropathology scores 1104 may be computed, by a pathology calculator 1110, from brain scans 1112 of the patient, e.g., performed by magnetic resonance imaging (MRI) or positron emission tomography (PET). PET scans, for example, can visualize beta-amyloid deposits in the brain, which form plaques found in Alzheimer patients.

To train the neurodegeneration prediction model 124, one or more predictive scores 126 are computed from the gait metrics 120 provided as part of the training data (in conjunction with the demographic patient data and personal health information 122), in the manner described with reference to FIG. 1, and evaluated against the cognitive and neuropathology scores 1102, 1104, using an evaluation module 1114 (e.g., implemented in software). The prediction model 124 and its parameters (e.g., network weights of an artificial neural network model, or probabilities associated with the branches in a decision tree), as well as the selection of the gait metrics 120 to be used in the computation of the predictive score(s) 126 can be adjusted iteratively based on the evaluation to reduce inconsistencies between the gait-based predictions and the cognitive and neuropathology scores 1102, 1104. The evaluation module 1114 may be part of, or accessed by, a suitable learning algorithm 1116 making the model adjustments (e.g., for a neural-network model, a gradient-descent-based backpropagation-of-errors algorithm, or some other learning algorithms known to those of ordinary skill in the art). Further, to determine gait metrics 120 that are good biomarkers for the condition of interest among a potentially larger set of initial gait metrics 120, feature reduction techniques known to those of ordinary skill in the art may be employed. The output of the training process is a trained neurodegeneration prediction model 124, along with a gait signature of metrics 120 on which the model operates.

Figure 12:
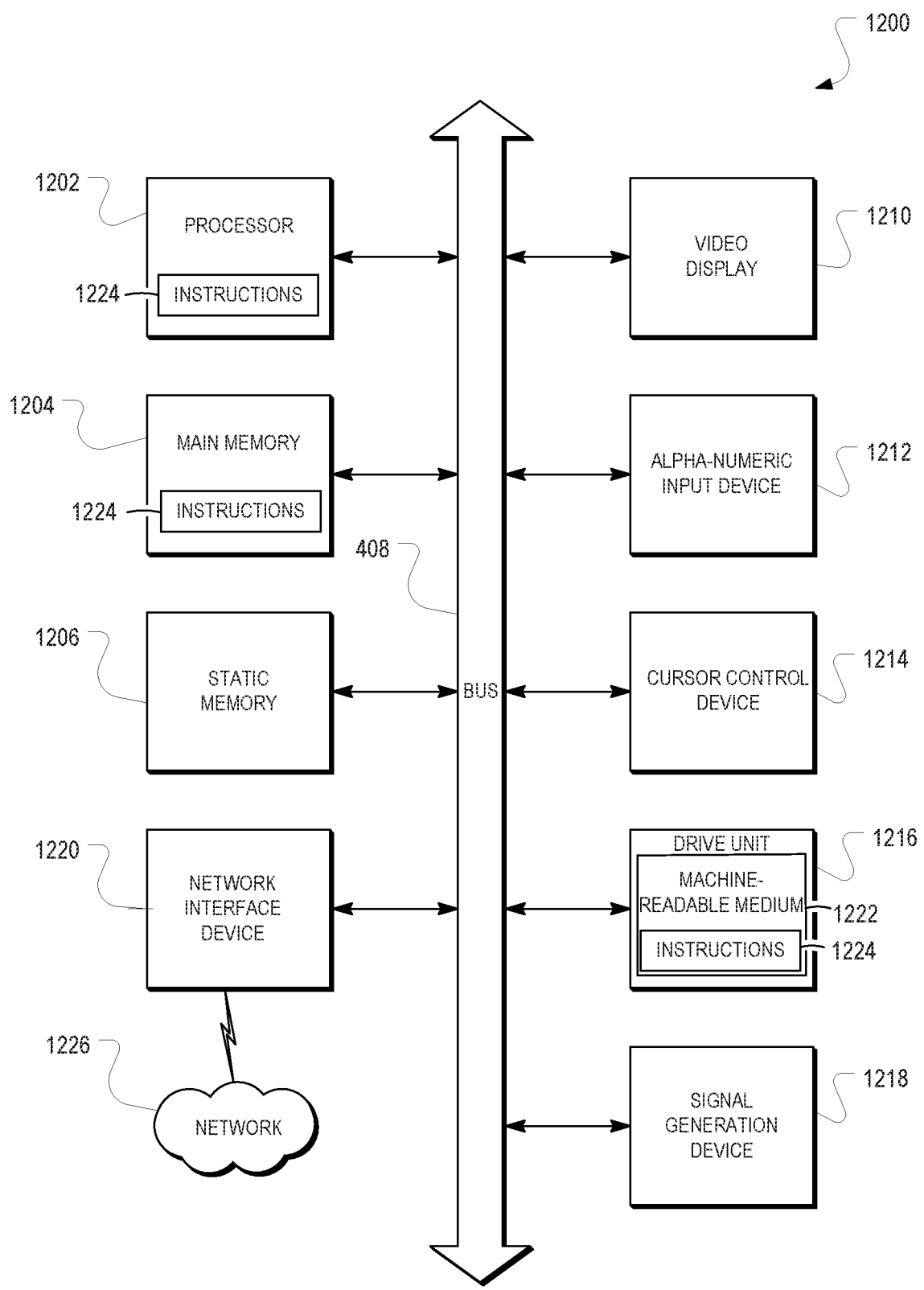
FIG. 12 is a block diagram illustrating an example computer system, in accordance with various embodiments, as can be used to implement any of the methods illustrated in FIGS. 1 and 9.

FIG. 12 is a block diagram of a machine in the example form of a computer system 600 within which instructions for causing the machine to perform any one or more of the methodologies discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. While only a single machine is illustrated, the term "machine" shall also be taken to include any collection of machines that individually or jointly execute a set (or multiple sets) of instructions to perform any one or more of the methodologies discussed herein. For example, those of ordinary skill in the art will understand that the various processing components depicted in FIG. 1 may be distributed over multiple computers or computer clusters, e.g., such that motion capture and computation of gait metrics takes place on one set of computers and the assessment of a neurodegenerative condition based on the gait metrics happens on another set of computers, at the same time or at a different time. Gait metrics may, for instance, be stored in a computer-readable medium for later diagnostic use.

The example computer system 1200 includes one or more processors 1202 (e.g., a central processing unit (CPU), a graphics processing unit (GPU) or both), a main memory 1204 and a static memory 1206, which communicate with each other via a bus 1208. The computer system 1200 may further include a video display unit 1210 (e.g., a liquid crystal display (LCD) or a cathode ray tube (CRT)). The computer system 1200 also includes an alphanumeric input device 1212 (e.g., a keyboard), a user interface (UI) navigation device 1214 (e.g., a mouse), a disk drive unit 1216, a signal generation device 1218 (e.g., a speaker), a network interface device 1220, and a data interface device 1228 (such as, e.g., an electrode interface).

The disk drive unit 1216 includes a machine-readable medium 1222 storing one or more sets of instructions and data structures (e.g., software) 1224 embodying or utilized by any one or more of the methodologies or functions described herein. The instructions 1224 may also reside, completely or at least partially, within the main memory 1204 and/or within the processor 1202 during execution thereof by the computer system 1200, the main memory 1204 and the processor 1202 also constituting machine-readable media.

While the machine-readable medium 1222 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding, or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; CD-ROM and DVD-ROM disks, or other data-storage devices. Further, the term "machine-readable medium" shall be taken to include a non-tangible signal or transmission medium, including an electrical signal, a magnetic signal, an electromagnetic signal, an acoustic signal and an optical signal.

The following numbered examples are illustrative embodiments:

1. A method for gait-based testing for a neurodegenerative condition in a patient, the method comprising: acquiring gait kinematic data for the patient; processing the gait kinematic data, using one or more computer processors, to derive one or more gait metrics collectively constituting a gait signature associated with the neurodegenerative condition; and operating a machine-learning model on input comprising the gait signature, using the one or more computer processors, to determine at least one predictive score associated with the neurodegenerative condition and the patient, the machine-learning model trained on a training dataset comprising gait metrics derived from kinematic data for a plurality of patients along with evaluation scores quantifying the neurodegenerative condition in the respective one of the plurality of patients.

2. The method of example 1, wherein the neurodegenerative condition comprises at least one of Alzheimer's disease, dementia, or heightened fall risk.

3. The method of example 1 or example 2, wherein the at least one predictive score comprises at least one of a likelihood that the neurodegenerative condition is present in the patient or a quantifier of the degree to which the neurodegenerative condition is present.

4. The method of any of example 1-3, wherein the evaluation scores comprise at least one of a cognitive score based on cognitive testing of the plurality of patients or neuropathology scores based on brain scans of the patients.

5. The method of any of examples 1-4, wherein the input to the machine-learning model further comprises patient demographic data or personal health information.

6. The method of any of examples 1-5, wherein the gait metrics collectively constituting the gait signature are a subset of a larger set of the gait metrics used in training the model.

7. The method of any of examples 1-6, wherein the gait metrics comprise an entropy metric.

8. The method of any of examples 1-7, wherein the gait kinematic data comprises at least one of time-series joint and body-segment kinematic parameters or spatiotemporal parameters derived therefrom.

9. The method of any of examples 1-8, wherein acquiring the gait kinematic data for the patient comprises processing video data of the patient taken as the patient was walking, using a machine-learning motion-analysis model.

10. The method of example 9, wherein the processing comprises detecting the patient in video frames of the video data, and cropping the frames to respective normalized regions containing the patient to generate processed video frames provided as input to the motion-analysis model.

11. The method of example 9 or example 10, wherein acquiring the gait kinematic data for the patient comprises determining three-dimensional joint center positions with the motion-analysis model, and postprocessing the 3D joint center positions to determine joint angles.

12. The method of example 11, wherein the postprocessing comprises at least one of filtering or removing outliers from time-dependent signals representing the joint center positions.

13. The method of example 11 or example 12, wherein the one or more gait metrics are computed from time-dependent signals representing the joint angles.

14. The method of any example 13, wherein computing the one or more gait metrics comprises detecting strides in the time-dependent signals and determining a variability between strides.

15. The method of any of examples 1-8, wherein acquiring the gait kinematic data for the patient comprises capturing marker-based data as the patient is walking, and processing the marker-based data with a biomechanical model.

16. A system for gait-based testing for a neurodegenerative condition in a patient, the system comprising: one or more cameras to capture video data of a patient walking; and one or more computer processors executing instructions stored in memory to perform operations comprising: processing the video data to compute gait kinematic data for the patient; processing the gait kinematic data to derive one or more gait metrics collectively constituting a gait signature associated with the neurodegenerative condition; and operating a machine-learning model on input comprising the gait signature to determine at least one predictive score associated with the neurodegenerative condition and the patient, the machine-learning model trained on a training dataset comprising gait metrics derived from kinematic data for a plurality of patients along with evaluation scores quantifying the neurodegenerative condition in the respective one of the plurality of patients.

17. The system of example 16, wherein the operations implement the method of any of examples 2-15.

18. A machine-readable medium storing instructions which, when executed by one or more hardware processors, cause the one or more hardware processors to perform operations for gait-based testing for a neurodegenerative condition in a patient, the operations comprising: processing gait kinematic data acquired for the patient to derive one or more gait metrics collectively constituting a gait signature associated with the neurodegenerative condition; and operating a machine-learning model on input comprising the gait signature to determine at least one predictive score associated with the neurodegenerative condition and the patient, the machine-learning model trained on a training dataset comprising gait metrics derived from kinematic data for a plurality of patients along with evaluation scores quantifying the neurodegenerative condition in the respective one of the plurality of patients.

19. The machine-readable medium of example 18, wherein the operations implement the method of any of examples 2-15.

20. A method for determining a gait signature of a patient based on video data of the patient walking, the method comprising: capturing the video data of the patient walking using one or more cameras; using one or more computer processors to perform operations comprising: preprocessing the video data using video-to-frame conversion, subject detection and tracking, and frame-to-subject cropping to generate processed video frames; operating a machine-learning model on the video data of the patient walking to determine three-dimensional joint positions, the machine-learning model having been trained on video training data correlated with ground-truth three-dimensional joint positions; calculating joint angles from the three-dimensional joint positions; and processing the joint angles to derive one or more gait metrics collectively constituting the gait signature.

22. The method of example 21, wherein the preprocessing comprises detecting the patient in video frames of the video data, and cropping the frames to respective normalized regions containing the patient to generate processed video frames provided as input to the machine-learning model.

23. The method of example 22, further comprising, prior to calculating the joint angles, at least one of filtering or removing outliers from time-dependent signals representing the three-dimensional joint positions.

24. The method of any of example 20-23, wherein the machine-learning model comprises a convolutional neural network and a Long Short Term Memory (LSTM) network.

25. A system for determining a gait signature of a patient based on video data of the patient walking, the system comprising: one or more cameras to capture video data of a patient walking; and one or more computer processors executing instructions stored in memory to perform operations comprising: preprocessing the video data using video-to-frame conversion, subject detection and tracking, and frame-to-subject cropping to generate processed video frames; operating a machine-learning model on the video data of the patient walking to determine three-dimensional joint positions, the machine-learning model having been trained on video training data correlated with ground-truth three-dimensional joint positions; calculating joint angles from the three-dimensional joint positions; and processing the joint angles to derive one or more gait metrics collectively constituting the gait signature.

26. The system of example 25, wherein the operations implement the method of any of examples 22-24.

27. A machine-readable medium storing instructions which, when executed by one or more hardware processors, cause the one or more hardware processors to perform operations for determining a gait signature of a patient based on video data of the patient walking, the operations comprising: preprocessing the video data using video-to-frame conversion, subject detection and tracking, and frame-to-subject cropping to generate processed video frames; operating a machine-learning model on the video data of the patient walking to determine three-dimensional joint positions, the machine-learning model having been trained on video training data correlated with ground-truth three-dimensional joint positions; calculating joint angles from the three-dimensional joint positions; and processing the joint angles to derive one or more gait metrics collectively constituting the gait signature.

28. The machine-readable medium of example 27, wherein the operations implement the method of any of examples 22-24.

Although the inventive subject matter has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A method for gait-based testing for a neurodegenerative condition in a patient, the method comprising:
processing video data of the patient walking to determine gait kinematic data for the patient, the gait kinematic data comprising time-dependent signals representing at least one of joint positions, joint angles, or body-segment rotations;
processing the gait kinematic data, using one or more computer processors, by segmenting the time-dependent signals by stride and deriving, from the segmented time-dependent signals, one or more gait metrics indicative of a degree of variability, between strides, in characteristic shapes of the time-dependent signals, the one or more gait metrics collectively constituting a gait signature associated with the neurodegenerative condition; and
operating a machine-learning model on input comprising the gait signature, using the one or more computer processors, to determine at least one predictive score associated with the neurodegenerative condition and the patient, wherein the machine-learning model has been trained on a training dataset comprising, for each of a plurality of patients, multiple gait metrics derived from gait kinematic data acquired for the respective patient, paired with one or more evaluation scores, including a neuropathology score derived from a brain scan of the respective patient, that quantify the neurodegenerative condition in the respective patient, and wherein the one or more gait metrics collectively constituting the gait signature have been selected from the multiple gait metrics in the course of training the machine-learning model by feature reduction.

2. The method of claim 1, wherein the neurodegenerative condition comprises at least one of Alzheimer's disease, dementia, or heightened fall risk.

3. The method of claim 1, wherein the at least one predictive score comprises at least one of a likelihood that the neurodegenerative condition is present in the patient or a quantifier of the degree to which the neurodegenerative condition is present.

4. The method of claim 1, wherein the one or more evaluation scores further comprise a cognitive score based on cognitive testing of the respective patient.

5. The method of claim 1, wherein the input to the machine-learning model further comprises patient demographic data or personal health information.

6. The method of claim 1, wherein the video data of the patient walking is processed using a machine-learning motion-analysis model.

7. The method of claim 6, wherein processing the video data comprises detecting the patient in video frames of the video data, and cropping the frames to respective normalized regions containing the patient to generate processed video frames provided as input to the motion-analysis model.

8. The method of claim 6, wherein processing the video data further comprises determining three-dimensional joint center positions with the motion-analysis model, and post-processing the 3D joint center positions.

9. The method of claim 8, wherein the postprocessing comprises at least one of filtering or removing outliers from time-dependent signals representing the joint center positions.

10. The method of claim 8, wherein the one or more gait metrics are computed from time-dependent signals representing the joint angles.

11. A system for gait-based testing for a neurodegenerative condition in a patient, the system comprising:
one or more cameras to capture video data of a patient walking; and
one or more computer processors executing instructions stored in memory to perform operations comprising:
processing the video data to compute gait kinematic data for the patient, the gait kinematic data comprising time-dependent signals representing joint angles or body-segment rotations;
processing the gait kinematic data by segmenting the time-dependent signals by stride and deriving, from the segmented time-dependent signals, one or more gait metrics indicative of a degree of variability between strides in characteristic shapes of the time-dependent signals, the one or more gait metrics collectively constituting a gait signature associated with the neurodegenerative condition; and
operating a machine-learning model on input comprising the gait signature to determine at least one predictive score associated with the neurodegenerative condition and the patient,
wherein the machine-learning model has been trained on a training dataset comprising, for each of a plurality of patients, multiple gait metrics derived from gait kinematic data acquired for the respective patient, paired with one or more evaluation scores, including a neuropathology score derived from a brain scan of the respective patient, that quantify the neurodegenerative condition in the respective patient, and
wherein the one or more gait metrics collectively constituting the gait signature have been selected from the multiple gait metrics in the course of training the machine-learning model by feature reduction.

12. The system of claim 11, wherein the neurodegenerative condition comprises at least one of Alzheimer's disease, dementia, or heightened fall risk.

13. The system of claim 11, wherein the video data is processed with a machine-learning motion-analysis model to compute the gait kinematic data.

14. The system of claim 11, wherein the one or more cameras consist of a single camera.

15. A non-transitory machine-readable medium storing instructions which, when executed by one or more hardware processors, cause the one or more hardware processors to perform operations for gait-based testing for a neurodegenerative condition in a patient, the operations comprising:
processing video data of the patient walking to determine gait kinematic data for the patient, the gait kinematic data comprising time-dependent signals representing at least one of joint angles or body-segment rotations;
processing the gait kinematic data acquired for the patient by segmenting the time-dependent signals by stride and deriving, from the segmented time-dependent signals, gait metrics indicative of a degree of variability between strides in characteristic shapes of the time-dependent signals, the gait metrics collectively constituting a gait signature associated with the neurodegenerative condition; and
operating a machine-learning model on input comprising the gait signature to determine at least one predictive score associated with the neurodegenerative condition and the patient,
wherein the machine-learning model has been trained on a training dataset comprising, for each of a plurality of patients, multiple gait metrics derived from gait kinematic data acquired for the respective patient, paired with one or more evaluation scores, including a neuropathology score derived from a brain scan of the respective patient, that quantify the neurodegenerative condition in the respective patient, and
wherein the one or more gait metrics collectively constituting the gait signature have been selected from the multiple gait metrics in the course of training the machine-learning model by feature reduction.

* * * * *